United States Patent
Hirata et al.

(10) Patent No.: US 6,869,626 B1
(45) Date of Patent: Mar. 22, 2005

(54) PRODUCTION METHOD OF ULTRAFINE GOLD PARTICLE-DISSOLVED WATER AND DEVICE THEREFOR

(75) Inventors: Yoshihiro Hirata, Kyoto (JP); Yoshio Ueda, Kyoto (JP); Hiraoki Takase, Kyoto (JP)

(73) Assignee: Phild Co., Ltd., Kyoto (JP)

( * ) Notice: Subject to any disclaimer, the term of this patent is extended or adjusted under 35 U.S.C. 154(b) by 232 days.

(21) Appl. No.: 10/130,123

(22) PCT Filed: Nov. 9, 2000

(86) PCT No.: PCT/JP00/07885
§ 371 (c)(1),
(2), (4) Date: Aug. 27, 2002

(87) PCT Pub. No.: WO01/36337
PCT Pub. Date: May 25, 2001

(30) Foreign Application Priority Data
Nov. 18, 1999 (JP) .......................... 11-327653

(51) Int. Cl.$^7$ ................................ A23L 2/00
(52) U.S. Cl. .............. 426/66; 210/321.6; 210/748; 204/277; 205/704; 205/751; 205/755; 426/590
(58) Field of Search ................ 210/177, 243, 210/259, 321.6, 500.23, 650, 748, 774, 791, 806; 426/66, 74, 590; 204/157, 263, 277, 278, 157.5; 205/704, 742, 751, 752, 755, 756

(56) References Cited

U.S. PATENT DOCUMENTS

| | | | | |
|---|---|---|---|---|
| 4,255,121 A | * | 3/1981 | Sugimoto | .................. 431/208 |
| 4,548,187 A | * | 10/1985 | Olsson et al. | ................ 123/557 |
| 5,061,459 A | * | 10/1991 | Bennett et al. | ................ 423/29 |
| 5,911,870 A | * | 6/1999 | Hough | ........................ 205/701 |
| 5,961,833 A | * | 10/1999 | Green et al. | ................ 210/638 |
| 6,045,704 A | * | 4/2000 | Sato et al. | .................. 210/694 |
| 6,315,886 B1 | * | 11/2001 | Zappi et al. | ................ 205/701 |

FOREIGN PATENT DOCUMENTS

| | | | |
|---|---|---|---|
| JP | 122682 | | 12/1937 |
| JP | 01-231876 | | 9/1989 |
| JP | 04-026701 | | 1/1992 |
| JP | 10-298615 | | 11/1998 |
| JP | 11-262377 | * | 9/1999 |

* cited by examiner

Primary Examiner—Joseph Drodge
(74) Attorney, Agent, or Firm—Knobbe, Martens, Olson & Bear LLP

(57) ABSTRACT

The present invention realized the production of a water product having excellent physiological activity such as health promoting activity and the utilization of the water, in which ultrafine gold particles having a diameter as small as 1–2 figures in micron order, much smaller than any ordinary fine gold particles, are dissolved.

According to the present invention, an aqueous ultrafine gold particle solution is produced using an apparatus comprising a pressure-resistant vessel equipped with a high-pressure water tank, a jet nozzle, an ignition device, and a combustion chamber, in which a gas mixture comprising hydrogen and oxygen is combusted in highly pressurized water, in which gold leaf fragments are suspended, and then the gold leaf fragments are heated and melted by the resulting combustion gas.

18 Claims, 4 Drawing Sheets

Flowchart for producing aqueous ultrafine gold particle solution

No. 200061655-001
June 30, 2000

ASSAY REPORT

Client Name: Phild Co., Ltd.

Specimen: GOLD WATER

Additional Remarks: ****

Incorporated Foundation
Japan Food Research Laboratories

| | |
|---|---|
| Tokyo H.Q. | 52-1, Motoyoyogi-machi, Shibuya-ku, Tokyo 151-0062 |
| Osaka Branch | 3-1, Toyotsu-cho, Suita-shi, Osaka 564-0081 |
| Nagoya Branch | 5-13, Ohsu 4-chome, Naka-ku, Nagoya 450-0011 |
| Kyushu Branch | 1-12, Shimogofuku-cho, Hakata-ku, Fukuoka 812-0034 |
| Tama Research Laboratory | 11-10, Nagayama 8-chome, Tama-shi, Tokyo 206-0025 |

The followings are analysis results for the above-identified specimen that was submitted to our laboratory on June 27, 2000.

| Assay Item | Results | Detection Limit | Notes | Analysis Method |
|---|---|---|---|---|
| Gold | 2.9mg/L | | | ICP Luminescence Analysis Method |

The End

ASSAY REPORT

Client Name: Phild Co., Ltd.

Specimen: GOLD AQUAMIRUM

Additional Remarks: ****

Incorporated Foundation
Japan Food Research Laboratories

| | |
|---|---|
| Tokyo H.Q. | 52-1, Motoyoyogi-machi, Shibuya-ku, Tokyo 151-0062 |
| Osaka Branch | 3-1, Toyotsu-cho, Suita-shi, Osaka 564-0081 |
| Nagoya Branch | 5-13, Ohsu 4-chome, Naka-ku, Nagoya 450-0011 |
| Kyushu Branch | 1-12, Shimogofuku-cho, Hakata-ku, Fukuoka 812-0034 |
| Tama Research Laboratory | 11-10, Nagayama 8-chome, Tama-shi, Tokyo 206-0025 |

The followings are analysis results for the above-identified specimen that was submitted to our laboratory on June 27, 2000.

| Assay Item | Results | Detection Limit | Notes | Analysis Method |
|---|---|---|---|---|
| Gold | 1.5 mg/L | | | ICP Luminescence Analysis Method |

The End

PRODUCTION METHOD OF ULTRAFINE GOLD PARTICLE-DISSOLVED WATER AND DEVICE THEREFOR

CROSS-REFERENCE TO RELATED APPLICATIONS

This is the National Phase under 35 U.S.C. § 371 of International Application No. PCT/JP00/07885, filed Nov. 9, 2000, which claims priority to Japanese Patent Application Nos. 11/327653 filed Nov. 18, 1999. The International Application was not published under PCT Article 21(2) in English.

FIELD OF THE INVENTION

The present invention relates to an aqueous drink in which ultrafine gold particles are dissolved, and more particularly to a process for producing an aqueous ultrafine gold particle solution, an apparatus therefor, and an aqueous health drink utilizing said aqueous solution.

BACKGROUND TECHNOLOGY

Since ancient times gold has been highly valued as the most important precious metal and mainly used in the form of ornaments or treasures. Recently, gold has also been recognized to be effective in promoting human health and used in a pure gold health bracelet, Japanese sake containing gold leaves, and the like. However, the effectiveness of these products in health is not sufficiently recognized although they are distinguished as luxury items containing expensive pure gold. Lately, in response to health-oriented social trends, health promoting effect of gold have again attracted an attention and it has been found that the health promoting effects are more remarkable in the form of gold ions or ultrafine gold particles than in the form of simple gold or gold leaves.

Potential of gold ions and fine gold particles being effective in promoting health or healing diseases has attracted a great deal of attention and a considerable contribution of gold to health has been known ("Golden Water Cures Intractable, Serious Diseases" by Tofu Takada). Therefore, further technological development, in particular in applied utilization of an aqueous solution or aqueous dispersion of gold ions or fine gold particles, is needed. However, several problems remain to be solved in implementation of such technology.

As mentioned above, water products containing fine gold particles are also known (ditto, page 64). However, in most products, gold leaves or gold powders are simply dispersed in water. It is extremely difficult to dissolve gold ions or fine gold particles in water and dissolution methods so far available are limited to those with the use of aqua regia or gold electrolyte.

In such conventional methods, requirements in terms of production cost and economic efficiency are not satisfied and moreover, technological problems such that health-promoting function cannot be fully exhibited remain to be solved.

In order to solve these problems in conventional methods and realize the potential of gold ions and fine gold particles being effective in promoting health or healing diseases, technological development in this field might be in progress. However, only a few techniques of this field have been disclosed in patent publications that are generally known to precisely reflect the progress in technological development, which indicates that potentiality in technological development in this field is still great.

The few disclosed prior arts mentioned above include Japanese Utility Model No. 304628 in which an organic antibacterial agent, such as antibacterial gold ions immobilized onto an ion exchange group of zeolite is admixed with an polyolefin mold resin in order to provide an antibacterial tank for drinking water that can prevent unwanted bacteria from invading through the wall of the tank and avert detrimental effect caused by chemicals dissolved without spoiling the flavor of the drinking water, Japanese Patent Application Laid-open No. H9-220580 in which in order to provide mineral water containing minerals, such as gold ions, that is useful in the human body, mineral carriers are suspended in water and then the minerals are released into water by stimulation by mineral release stimulating means, such as acid addition and electrolysis; Japanese Patent Application Laid-open No. H9-10772 in which in order to produce an inexpensive bactericide, antiseptic water having excellent bactericide activity, a heavy metal such as gold is dissolved into acidic ionic water having a pH 2.6 to 4.5 produced using an electrolytic water purification system or oxidation potential water having a pH lower than 2.7; and Japanese Patent Application Laid-open No. H5-280841 in which in order to produce a health ice product having foreign matters, such as gold leaves, evenly dispersed in an ice block, gold leaves are evenly admixed with crushed granular ice while stirring, the granular ice mixed with the foreign matter is packed into an ice-making can, and water is gradually injected from the bottom of the ice-making can to form ice.

However, virtually all of these conventional techniques enclosed are far from suitable means to solve the above-mentioned problems and cannot basically solve the problems, although the technique disclosed in Japanese Patent Application Laid-open No. H9-10772 is noticeable, in which in order to provide mineral water containing minerals, such as gold ions, that is useful in the human body, mineral carriers are suspended in water and then the minerals are released into water by stimulation by mineral release stimulating means, such as acid addition and electrolysis.

Utilization of activity of gold ions and fine gold particles in physiologically active materials, health food materials and pharmaceuticals is important as technology directly related to everyday life. Their application will become more frequent in future and thus the development of technology in this field is highly expected.

Accordingly, the present inventors intensively studied the process of producing health water containing ultrafine gold particles in prospect of possibility that health can be promoted in extremely simple way and various symptoms can be improved by drinking water containing gold ions or fine gold particles, and thus completed the present invention.

DISCLOSURE OF THE INVENTION

As mentioned above, potential of gold ions and fine gold particles being effective in promoting health or healing diseases is great and further technological development has been expected. Possible basic applied forms can be an aqueous solution or aqueous dispersion of gold ions or fine gold particles; however, several problems remain to be solved to implement these forms. For example, it is extremely difficult to dissolve gold ions or fine gold particles in water and only methods so far available are to admixing of gold leaves or gold powders with water or to use gold electrolyte. However, in such conventional methods, technological problems, such that requirements in terms of production cost and economic efficiency are not satisfied, that health promoting function cannot be fully exhibited, and that safeness of using chemical electrolyte to the human body is not confirmed, remain to be solved.

Thus, although utilization of gold ions and fine gold particles for use in physiologically active materials, health food materials and pharmaceuticals has been highly expected, concrete technology has not been satisfactorily developed.

Accordingly, an objective of the present invention is to solve the above-mentioned problems to provide an aqueous solution of gold ions and fine gold particles and then utilize the resulting solution in the field of health promotion.

The present invention is to contribute to the technological development and implementation of application for effective use of gold ions and fine gold particles by solving the abovementioned problems and thus develop a novel process for producing an aqueous fine gold particle solution, an apparatus therefor, and an aqueous health drink utilizing the aqueous fine gold particle solution.

The present invention is greatly characterized in that an aqueous ultrafine gold particle solution is produced by combusting a gas mixture comprising hydrogen and oxygen in highly pressurized water in which gold leaf fragments are suspended and then heating and melting the gold leaf fragments by the resulting combustion gas to melt them, and made into an aqueous health drink. A test by monitors confirmed that the water actually obtained according to the present invention has a marked effect in improving physical conditions and recovering from fatigue.

In the present invention, an aqueous solution of fine gold particles means water in which ultrafine gold particles look like being dissolved seemingly and it does not mean water in which gold powders or gold leaves are simply suspended.

The present invention basically comprises the following (1) to (7).

(1) An aqueous ultrafine gold particle solution produced by combusting a gas mixture comprising oxygen and hydrogen in highly pressurized water, in which gold leaf fragments are suspended, and then heating the gold leaf fragments by the resulting combustion gas.

(2) A method of producing an aqueous ultrafine gold particle solution comprising combusting a gas mixture comprising oxygen and hydrogen in highly pressurized water, in which gold leaf fragments are suspended, and then heating the gold leaf fragments by the resulting combustion gas.

(3) An apparatus for producing an aqueous ultrafine gold particle solution comprising a pressure-resistant vessel equipped with a highly pressurized water tank, a jet nozzle for a gas mixture comprising hydrogen and oxygen, an ignition device, and a combustion chamber.

(4) The apparatus for producing an aqueous ultrafine gold particle solution described in (3) above further comprising a water electrolysis system for producing a gas mixture comprising hydrogen and oxygen.

(5) The apparatus for producing an aqueous ultrafine gold particle solution described in (3) or (4) above further comprising a filtering system for removing remaining gold leaf fragments and fine gold particles.

(6) The apparatus for producing an aqueous ultrafine gold particle solution described (3), (4), or (5) above in which the precipitate of fine gold particles remaining in the filtering system is washed and recovered by backwash of the filtering system.

(7) A health water product comprising an aqueous ultrafine gold particle solution.

BRIEF DESCRIPTION OF THE DRAWINGS

FIG. 3 shows results of analysis of gold in water in which ultrafine gold particles are dissolved using distilled water.

FIG. 4 is a result of analysis of gold in water in which ultrafine gold particles are dissolved using tap water.

EXPLANATION OF SYMBOLS

Figure 1:
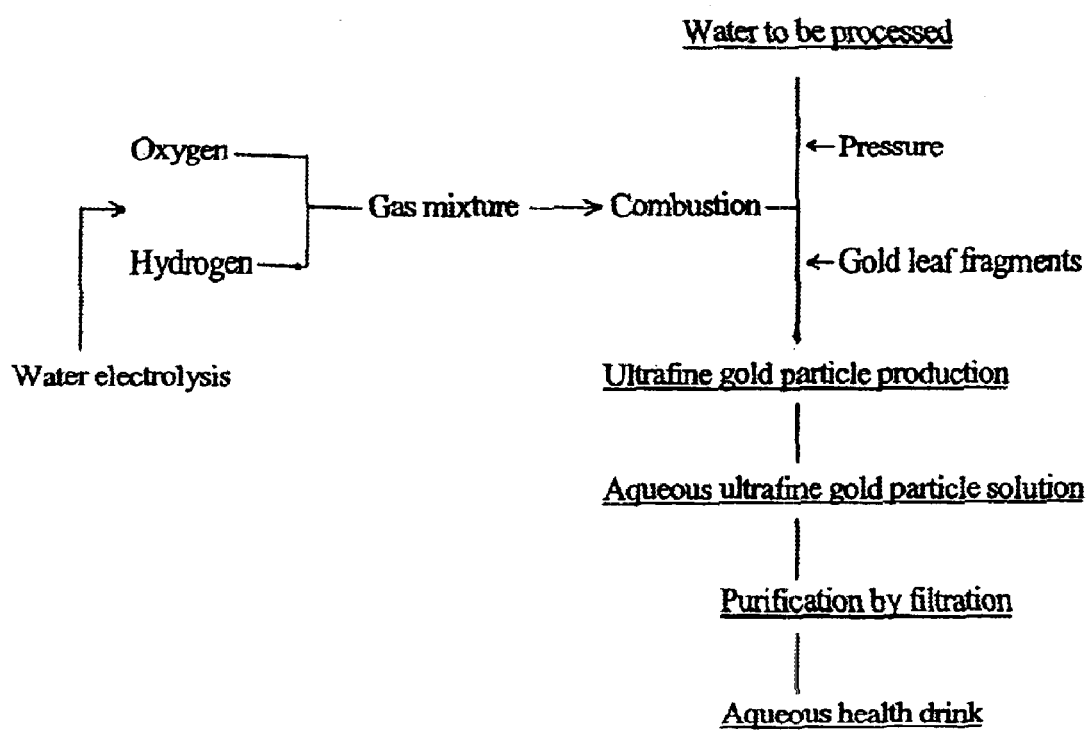
FIG. 1 is a flowchart showing summary of the process of the present invention.

1: Apparatus for producing an aqueous ultrafine gold particle solution
2: High-pressure tank
3: Pressurized water
4: Gold leaf fragment
5: Jet nozzle
6: Gas mixture
7: Combustion chamber
8: Opening for water supply
9: Route for hydrogen supply
10: Route for oxygen supply
11: Stirring device
12: Ignition device
13: Pump
14: Filtering system
15: Product
16: Water electrolysis system
17: Electrolysis vessel
18: Water
19: Electrode plate
20: Power source.

BEST MODE OF CARRYING OUT THE INVENTION

Conventionally, an aqueous gold ion solution is generally produced by using an electrolyte known to be used for gold plating, which is poor in ion generation efficiency, and furthermore, the resulting product can be hazardous to the human body and thus its use is limited. On the other hand, gold particles are insoluble in water, therefore, when fine gold particles are dispersed in water, their total surface area is small for the weight of the gold mixed, which results in poor cost efficiency. Thus this kind of methods is technologically unsatisfactory.

Accordingly, the present inventors intensively studied the improvement of these conventional techniques and considered that the abovementioned methods with various problems can be improved by dissolving ultrafine gold particles that are finer than conventional fine particles, and thus conducted research on methods for producing an aqueous ultrafine gold particle solution. As a result of repeated trial and error, the present inventors accomplished a novel method in which a gas mixture comprising hydrogen and oxygen is combusted in highly pressurized water and then gold leaf fragments are heated by the resulting combustion gas, and thus completed the present invention.

The present invention is to realize the production and utilization of water in which ultrafine gold particles having a diameter as small as 1–2 figures in micron order, much smaller than any of the abovementioned conventional fine gold particles, are dissolved. This water product is furthermore improved in its high functions, such as health promoting activity, than water products in which gold leaves or fine gold particles are suspended, and is confirmed to be characteristically as safe as ordinary water.

A primary feature of the present invention is a process for producing an aqueous ultrafine gold particle solution in which a gas mixture comprising hydrogen and oxygen is combusted in highly pressurized water in which gold leaf fragments are suspended and then the gold leaf fragments are heated by the resulting combustion gas. FIG. 1 shows a summary of this process.

Figure 2:
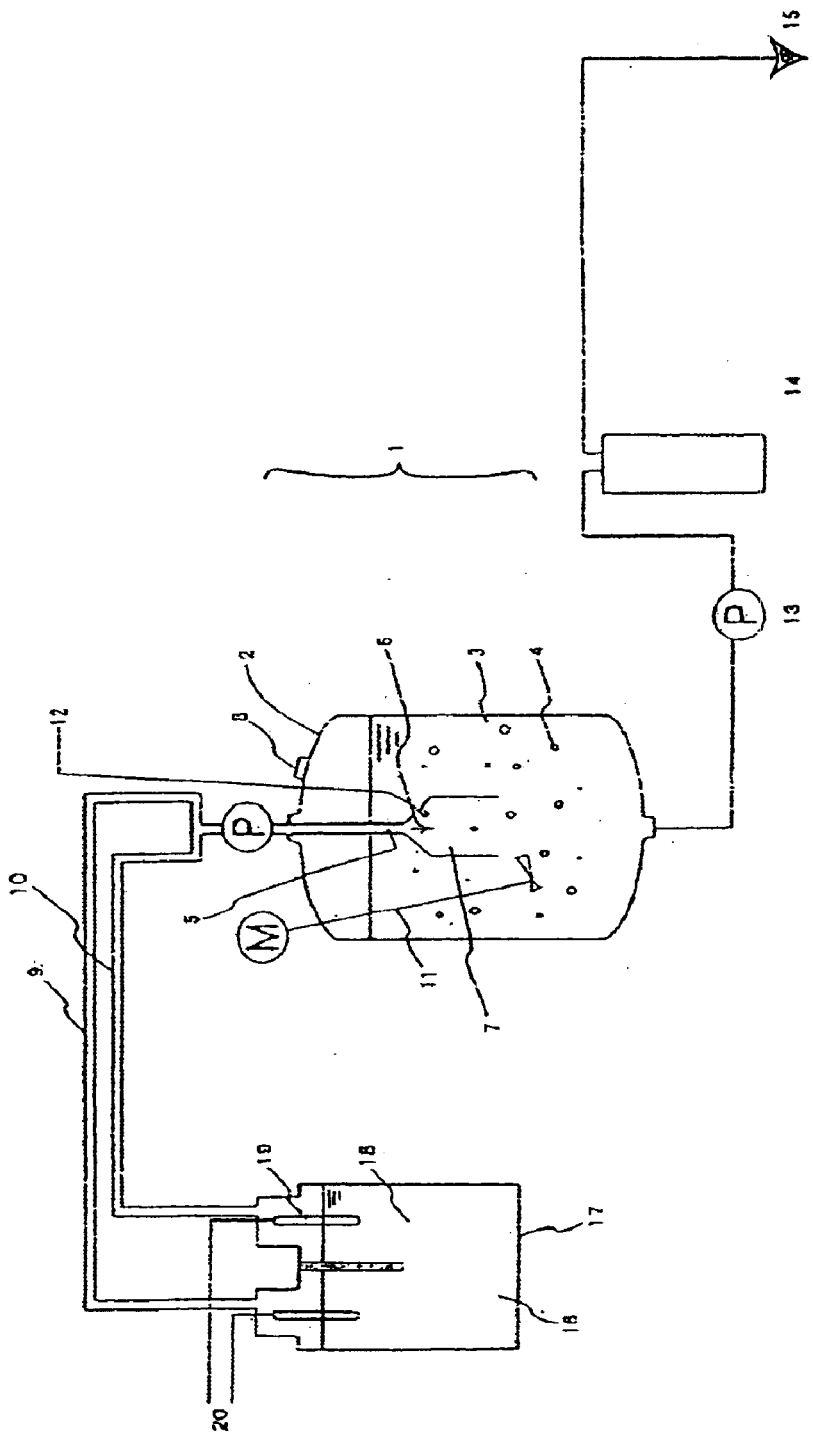
FIG. 2 is a schematic illustration of an apparatus for producing an aqueous ultrafine gold particle solution according to the present invention.

Further, the present invention further developed an apparatus to implement a method for producing an aqueous solution in which ultrafine gold particles are dissolved. FIG. 2 shows the apparatus for the production.

In a basic production process of the present invention, water is poured into a pressure tank and gold leaf fragments are admixed and suspended while stirring, after which the water is pressurized under high pressure, a gas mixture comprising hydrogen and oxygen is injected from a nozzle and then completely combusted until it reaches the state of ultrahigh temperature vapor gas combustion, so that the gold leaf fragments are instantaneously dissolved and dispersed in water in the combustion gas. At this moment, ultrafine gold particles having a size as extremely small as microns are generated and are in the state of apparently being dissolved rather than being suspended. Combustion in water can be most effective and stable with a gas mixture comprising hydrogen and oxygen. This stable combustion requires high pressure.

Further, no physical or chemical explanation has been given why the gold leaf fragments are instantaneously dissolved in the combusting gas in highly pressurized water to become ultrafine particles.

The water thus produced can be used as it is without filtration, or depending on the use, it can be filtered with a filter or the like to remove remaining gold leaf fragment and a small mount of fine gold particles larger than ultrafine gold particles, thereby obtaining an aqueous solution in which only ultrafine particles are dissolved. Gold leaf fragments and fine gold particles remaining on the filter as precipitate are recovered for reuse by appropriate backwash, which improve economical efficiency.

Supply of hydrogen and oxygen gases in the method of the production according to the present invention has to be precisely controlled to maintain the hydrogen-oxygen rate to be 2 to 1. It is also necessary to control the reaction time and the amount of fuel to be combusted. The resulting water may have no desired effect if the reaction time is too short, while the taste as aqueous water may be spoiled if the reaction time is too long.

An apparatus for producing a gold health water product of the present invention in FIG. 2 constitutes an apparatus 1 for producing an aqueous solution in which ultrafine gold particles are dissolved comprising a high-pressure tank 2, a jet nozzle 5 for a gas mixture comprising oxygen and hydrogen, and a combustion chamber 7. In addition, a water electrolysis system 16 to provide materials for a gas mixture, i.e., hydrogen and oxygen, and a filtering system 14 to filter the resulting aqueous solution are installed.

A production vessel of the present invention is a pressure-resistant tank (high-pressure tank) 2 made of metal, preferably stainless steel, into which water to make pressurized water 3 is supplied through an opening 8 and at the same time gold leaf fragments 4 are admixed, and the admixture is stirred by a stirring device 11 operated by an electric motor.

A combustion chamber 7 is made so as to surround a jet nozzle 5 for a gas mixture 6 consisting of hydrogen and oxygen supplied through a hydrogen supply route 9 and an oxygen supply route 10. Here, the gas mixture is ignited by an ignition device 12 and then completely combusted until it reaches the state of ultrahigh temperature vapor gas combustion, so that the gold leaf fragments are instantaneously dissolved with the resulting combusting gas to produce an aqueous solution in which ultrafine gold particles are dissolved in water.

The aqueous solution thus obtained can be used as it is or run through a filter housing (filtering device) 14 using a pump 13 and is released as a product 15. As a filter, in order to filter only ultrafine particles, a hollow fiber filter having a pore size of micron order rather than an ion exchange membrane or a reverse osmotic membrane is preferably used.

As for the scale of production of the present invention, one ton of aqueous solution can be produced by injecting a gas mixture at a rate of about 5 liters per second for about 2 hours, in which 40–60 g of gold powders are previously dispersed in one ton of water. Further, too much pressure may cause destruction of the apparatus, while too little pressure may blow up the gas from the nozzle and the heated gold leaf fragments are wrapped in the resulting foams and released on the surface of water, which results in poor generation of ultrafine gold particles. In this case, preferable pressure is about 3.5 atom. The pressure of highly pressurized water in the pressure tank is set to about 2 atom.

Further, in the apparatus of the present invention, it is also possible to use material gas supply cylinders in place of a water electrolysis system 16 to provide hydrogen and oxygen to be used as fuel. However, hydrogen and oxygen provided by water electrolysis are pure materials and thus the material hydrogen and oxygen can be readily supplied.

The water electrolysis system 16 can be an ordinary system composed of electrolysis vessel 17 containing water 18 and electrode plates 19, 20 connected to a power source 20.

Acidic or alkaline material water is electrolyzed to generate oxygen gas at the anode and hydrogen gas at the cathode, which are used as material gases for combustion.

Further in the present invention, a filter housing 14 is preferably added when remaining gold leaf fragments and gold particles in the resulting aqueous solution have to be removed. Water produced by this apparatus can be filtered with a filter or the like depending on the use to remove remaining gold leaf fragments and a trace of fine gold particles larger than ultrafine gold particles, thereby obtaining an aqueous solution in which only ultrafine particles are dissolved. Gold leaf fragments and fine gold particles remaining on the filter as precipitate are recovered by backwash for reuse, which contributes to cost-effectiveness.

Furthermore, the present invention comprises an aqueous health drink comprising an aqueous solution in which ultrafine gold particles are dissolved in water, which is produced by using the abovementioned method and apparatus. As mentioned above, purification is carried out through the filter housing 14 equipped with a hollow fiber membrane having a pore size of micron order and thus remaining gold leaf fragments and fine gold particles are appropriately filtered out to make an aqueous health drink. By such filtration, an aqueous drink that meets with the Food Hygienic Standard can be obtained. Filtration can be carried out, for example, using a series of hollow fiber membranes in order, each having a pore size of 50 microns, 25 microns, 3 microns, 0.5 micron, and 0.1 micron, in which the first membrane is placed where the resulting fluid is released from the reaction tank.

Aqueous health drinks obtained according to the present invention were analyzed by a third-party institution (Japan Food Research Laboratories, Foundation). Results are shown in FIGS. 3 and 4.

FIG. 3 shows the gold content in a sample in which distilled water was used as pressurized water into which gold leaf fragments were admixed and the gold leaf fragments were dissolved using hydrogen and oxygen generated by water electrolysis as fuel. FIG. 3 shows the gold content in a sample in which tap water was used as pressurized water into which gold leaf fragments were admixed and the gold leaf fragments were dissolved using hydrogen and oxygen generated by water electrolysis as fuel.

An aqueous health drink obtained in the present invention is believed to become an epoch-making drink to sufficiently meet the demands in current health-oriented society. Although it is not clear at the moment why an aqueous solution in which ultrafine gold particles are dissolved has effectiveness to health and what kind of physiological activity is involved, marked effects in improving physical conditions and recovering from fatigue were observed when samples were tested by monitors as described below, and thus actual effectiveness was confirmed. Stability in the body and physiological effects such as intestinal absorbability were fully exhibited probably owing to ion emission effect and extremely large active surface area of ultrafine gold particles, or characteristics of gold itself as a precious metal, and further chemical and physical stability of gold.

The embodiments of the present invention are further illustrated by the following examples with the accompanying drawings that are not intended as a limitation of the invention.

EXAMPLE

FIG. 2 is an apparatus 1 for producing an aqueous solution in which ultrafine gold particles are dissolved comprising a high-pressure tank 2, a jet nozzle 5 for a gas mixture consisting of hydrogen and oxygen, and a combustion chamber 7 for the gas mixture.

Detailed operations are as follows. A production vessel of the present invention is a pressure-resistant tank 2 made of metal, preferably stainless steel, into which water to make pressurized water 3 is supplied through an opening 8, at the same time gold leaf fragments 4 are admixed, and the admixture is stirred by a stirring device 11 operated by an electric motor.

A combustion chamber 7 is made so as to surround a jet nozzle 5 for a gas mixture 6 consisting of hydrogen and oxygen supplied through a hydrogen supply route 9 and an oxygen supply route 10. The gas mixture is ignited by an ignition device 12 and completely combusted until it reaches ultrahigh temperature vapor gas combustion state, so that the gold leaf fragments is instantaneously dissolved with the resulting combustion gas to produce an aqueous solution in which ultrafine gold particles are dissolved in water. The aqueous solution thus obtained is appropriately run through the filter housing 14 using a pump 13 and is released as a product 15.

Conditions for Operation

Pressurized water water 1 ton (2 atom)
Gas mixture: 5 liters/sec (3.5 atom)
Injection time: 2 hours
Gold leaf fragment supply: 50 g
Aqueous solution produced: about 1 ton.

The resulting aqueous solution is filtered through a series of hollow fiber membranes in order, each having a pore size of 50 microns, 25 microns, 3 microns, 0.5 micron, and 0.1 micron to obtain an aqueous health drink in which ultrafine gold particles are dissolved.

Drink Test of Aqueous Health Drink

An aqueous health drink in which ultrafine gold particles were dissolved was given to ten adult male and female monitors to confirm its effect and efficacy in improving health and healing diseases.

Amount of Drink, Number of Monitors, and Response

| Volume per day: | |
|---|---|
| About 1 cup | 5 |
| Up to 3 cups | 2 |
| More than 4 cups | 3 |
| Taste/flavor: | |
| Good | 9 |
| Tasteless | 1 |
| Odor: | |
| Unnoticeable | 9 |
| Noticeable | 1 |
| Confirmation of efficacy | |
| 5 out of 10 reported effectiveness | ⊚ |
| 3 out of 10 reported effectiveness | ○ |
| 1 out of 10 reported effectiveness | Δ |
| All 10 reported ineffectiveness | x |

Water for Comparison (Comparative Example):

A mixture of gold leaves and fine gold particles having an average diameter of 1 mm according to a conventional method was used (10 mg gold/10 cc). The test was carried out by another group of 10 male and female monitors other than the above-mentioned monitors.

Table 1 shows results of the test carried out under the abovementioned conditions by the monitors using the water of the present invention and water for comparison.

TABLE 1

| Observation | Present invention | Comparison |
|---|---|---|
| Physical conditioning | ⊚ | Δ |
| Recovery from fatigue | ⊚ | Δ |
| Stimulating appetite | ○ | x |
| Bowel conditioning | ⊚ | Δ |
| Lowering blood pressure | ⊚ | x |
| Healing gastritis | ○ | x |
| Recovery from eyestrain | ○ | x |

According to the results shown in Table 1, the drink of the present invention was reported to be palatable in terms of taste and order by most of the monitors and was confirmed to have marked effect in improving physical conditions, health, and physical functions.

Potential for Industrial Use

As mentioned above, the present invention is to provide a novel method for producing an aqueous ultrafine gold particle solution, an apparatus therefor, and an aqueous health drink utilizing the aqueous ultrafine gold particle solution, which makes it possible to obtain the aqueous ultrafine gold particle solution easily and at low cost and to effectively contribute to health improvement by conditioning physical conditions and stimulating appetite by making the aqueous ultrafine gold particle solution into an aqueous heal drink utilizing physiological activity of the ultrafine gold particles.

What is claimed is:

1. A portable aqueous ultrafine gold particle solution comprising ultrafine gold particles having a diameter on the order of ones to tens of microns, said solution being produced by combusting a gas mixture comprising oxygen and hydrogen in highly pressurized water, in which gold leaf fragments are suspended, and then heating and melting the gold leaf fragments by the resulting combustion gas.

2. An aqueous health drink comprising an aqueous ultrafine gold particle solution according to claim 1.

3. A method of producing an aqueous ultrafine gold particle solution comprising combusting a gas mixture comprising oxygen and hydrogen in highly pressurized water, in which gold leaf fragments are suspended, and then heating and melting the gold leaf fragments by the resulting combustion gas to obtain an aqueous ultrafine gold particle solution.

4. The method of producing an aqueous ultrafine gold particle solution according to claim 3, further comprising removing the remaining gold leaf fragments from the aqueous ultrafine gold particle solution.

5. The method of producing an aqueous ultrafine gold particle solution according to claim 3, wherein the highly pressurized water comprises 40–60 g of gold leaf fragments based on one ton of water.

6. An apparatus for producing an aqueous ultrafine gold particle solution comprising a highly pressurized closed water tank, a single jet nozzle having a single path disposed inside the water tank for a gas mixture comprising hydrogen and oxygen, a combustion chamber connected to the single jet nozzle, and an ignition device in the vicinity of the combustion chamber.

7. The apparatus for producing an aqueous ultrafine gold particle solution according to claim 6 further comprising a filtering system for removing remaining gold leaf fragments and fine gold particles.

8. The apparatus for producing an aqueous ultrafine gold particle solution according to claim 7, in which the precipitate of fine gold particles remaining in the filtering system is washed and recovered by backwash of the filtering system.

9. The apparatus according to claim 6, wherein the water tank has a bottom provided with an outlet.

10. The apparatus according to claim 6, further comprising a water electrolysis system for producing the gas mixture comprising hydrogen and oxygen.

11. An apparatus for producing an aqueous ultrafine gold particle solution comprising (i) a pressure-resistant vessel equipped with a highly pressurized water tank, a jet nozzle for a gas mixture comprising hydrogen and oxygen, an ignition device, and a combustion chamber and (ii) a water electrolysis system for producing said gas mixture comprising hydrogen and oxygen.

12. The apparatus for producing an aqueous ultrafine gold particle solution according to claim 11 further comprising a filtering system for removing remaining gold leaf fragments and fine gold particles.

13. An apparatus for producing an aqueous ultrafine gold particle solution comprising (i) a pressure-resistant vessel equipped with a highly pressurized water tank, a jet nozzle for a gas mixture comprising hydrogen and oxygen, an ignition device, and a combustion chamber and (ii) a filtering system for removing remaining gold leaf fragments and fine gold particles, wherein the filtering system comprises a hollow fiber filter having a pore size of micron order.

14. A method of producing an ultrafine gold particle-dissolved aqueous solution, comprising the steps of:

dispersing gold leaf fragments in water;

pressurizing the water in a reaction tank;

introducing a gas mixture of oxygen and hydrogen into the pressurized water; and combusting the gas mixture in the pressurized water to heat and melt the gold leaf fragments by the burning reaction of oxygen and hydrogen, thereby pulverizing the gold leaf fragments in the water.

15. An apparatus for producing an ultrafine gold particle-dissolved aqueous solution, comprising:

a closed pressure tank for pressurizing and storing water containing gold leaf fragments;

a single jet nozzle having a single path provided in the tank for introducing a gas mixture of hydrogen and oxygen into pressurized water when stored in the tank;

a combustion chamber provided in the tank in the vicinity of the jet nozzle where a burning reaction of hydrogen and oxygen takes place in the pressurized water when stored in the tank; and an ignition device provided in the combustion chamber for igniting the gas mixture introduced from the jet nozzle to cause a burning reaction of hydrogen and oxygen in the pressurized water when stored in tank, wherein the gold leaf fragments are heated and melted by the burning reaction of oxygen and hydrogen, thereby pulverizing the gold leaf fragments in the water.

16. The apparatus according to claim 15, further comprising a water electrolysis system for producing said gas mixture of hydrogen and oxygen.

17. A portable aqueous ultrafine gold particle solution comprising ultrafine gold particles having a diameter on the order of ones to tens of microns, said solution being produced by combusting a gas mixture comprising oxygen and hydrogen in highly pressurized water, containing gold.

18. A portable aqueous ultrafine gold particle solution comprising ultrafine gold particles having a diameter on the order of ones to tens of microns, said solution being produced by a process comprising treating a suspension containing gold leaf fragments.

* * * * *

UNITED STATES PATENT AND TRADEMARK OFFICE
CERTIFICATE OF CORRECTION

PATENT NO. : 6,869,626 B1 Page 1 of 1
DATED : March 22, 2005
INVENTOR(S) : Yoshihiro Hirata, Yoshio Ueda and Hiroaki Takase It is certified that error appears in the above-identified patent and that said Letters Patent is hereby corrected as shown below:

Column 9,
Line 8, delete "portable" and insert -- potable --.

Column 10,
Lines 47 and 52, delete "portable" and insert -- potable --.
Lines 49-50, after "produced by" insert -- a process comprising --.

Signed and Sealed this

Thirteenth Day of June, 2006

JON W. DUDAS
*Director of the United States Patent and Trademark Office*